(12) United States Patent
Dröge

(10) Patent No.: US 11,573,215 B2
(45) Date of Patent: Feb. 7, 2023

(54) ANALYSIS OF GAS IN DRILLING FLUIDS

(71) Applicant: Halliburton Energy Services, Inc., Houston, TX (US)

(72) Inventor: Markus Bernhard Dröge, Rogaland (NO)

(73) Assignee: Halliburton Energy Services, Inc., Houston, TX (US)

( * ) Notice: Subject to any disclaimer, the term of this patent is extended or adjusted under 35 U.S.C. 154(b) by 268 days.

(21) Appl. No.: 16/765,593

(22) PCT Filed: Jan. 19, 2018

(86) PCT No.: PCT/US2018/014577
§ 371 (c)(1),
(2) Date: May 20, 2020

(87) PCT Pub. No.: WO2019/143362
PCT Pub. Date: Jul. 25, 2019

(65) Prior Publication Data
US 2020/0308963 A1 Oct. 1, 2020

(51) Int. Cl.
*G01N 30/88* (2006.01)
*B01D 19/00* (2006.01)
*E21B 21/06* (2006.01)
*G01N 33/28* (2006.01)
*E21B 47/06* (2012.01)
(Continued)

(52) U.S. Cl.
CPC ......... *G01N 30/88* (2013.01); *B01D 19/0063* (2013.01); *B01D 19/0068* (2013.01); *E21B 21/067* (2013.01); *G01N 33/2823* (2013.01);
*E21B 47/06* (2013.01); *E21B 49/005* (2013.01); *E21B 49/088* (2013.01)

(58) Field of Classification Search
CPC ... G01N 30/88; G01N 33/2823; E21B 21/067
USPC ...................................... 73/152.19
See application file for complete search history.

(56) References Cited

U.S. PATENT DOCUMENTS

| 4,635,735 A | 1/1987 | Crownover |
| 2011/0219853 A1* | 9/2011 | Henderson ......... B01D 19/0063 96/204 |

(Continued)

FOREIGN PATENT DOCUMENTS

| EP | 2796663 A2 | 10/2014 |
| EP | 3336538 A1 | 6/2018 |

(Continued)

OTHER PUBLICATIONS

International Search Report and Written Opinion dated Oct. 16, 2018 for PCT Application No. PCT/US2018/014577 filed Jan. 19, 2018, (14 pgs).

*Primary Examiner* — John Fitzgerald
*Assistant Examiner* — Rodney T Frank
(74) *Attorney, Agent, or Firm* — K&L Gates LLP

(57) ABSTRACT

A system and method for analyzing a gas in a drilling fluid involves a degasser operable to separate the gas from the drilling fluid. A gas analyzer in fluid communication with the degasser receives a sample of the separated gas and determines a property of the gas. A controller in communication with the gas analyzer automates the operation of the gas analyzer by adjusting a parameter of the separated gas sample as the gas sample is supplied to the gas analyzer.

20 Claims, 9 Drawing Sheets

(51) Int. Cl.
*E21B 49/00* (2006.01)
*E21B 49/08* (2006.01)

(56) References Cited

U.S. PATENT DOCUMENTS

| | | |
|---|---|---|
| 2013/0270006 A1 | 10/2013 | Selman et al. |
| 2013/0275047 A1 | 10/2013 | Selman et al. |
| 2016/0032720 A1 | 2/2016 | Schexnaider |
| 2016/0084023 A1 | 3/2016 | Calleri |
| 2016/0153955 A1 | 6/2016 | Strapoc et al. |
| 2017/0266654 A1* | 9/2017 | Sanroma ............ G01N 35/1095 |

FOREIGN PATENT DOCUMENTS

| | | |
|---|---|---|
| WO | 2012052962 A1 | 4/2012 |
| WO | 2017069765 A1 | 4/2017 |

* cited by examiner

ANALYSIS OF GAS IN DRILLING FLUIDS

BACKGROUND

This section is intended to provide relevant background information to facilitate a better understanding of the various aspects of the described embodiments. Accordingly, it should be understood that these statements are to be read in this light and not as admissions of prior art.

Modern petroleum drilling and production operations demand a great quantity of data and information relating to downhole conditions and drilling and production parameters. Such information typically includes characteristics of the earth formations traversed by a wellbore, as well as data relating to the size and configuration of the borehole itself. The collection of information relating to downhole conditions, commonly referred to as "logging", can be performed by a variety of methods.

During drilling operations, a fluid known as drilling mud or drilling fluid is normally pumped down drill string, and circulated up the annular space which is formed between drill string and the internal surface of the wellbore. The basic functions of drilling mud are: (1) to cool and lubricate the drill bit and downhole equipment during drilling operations; (2) to transport pieces of drilled-up rock and other debris from the bottom of the hole to the surface; (3) to suspend such rock and debris during periods when circulation is stopped; (4) to provide hydrostatic pressure to control encountered subsurface pressures; and (5) to seal the porous rock in the well with an impermeable filter cake.

As circulated drilling mud returns to the Earth's surface and is pumped out of a well, the mud often contains pieces of broken, drilled-up rock and other solid debris known as "cuttings" or "drill cuttings". In most cases, an effluent mud stream flowing out of a well, together with associated drill cuttings, is directed to one or more devices which are specifically designed to separate such drill cuttings from the mud. Such devices include, but are not limited to, "shale shakers," desanders, desilters, hydrocyclones and centrifuges.

"Mud logging" involves the monitoring and assessment of downhole conditions derived from analyzing cuttings and formation fluids (e.g., brine, water, hydrocarbon gas, or oil) carried with the drilling fluid from the formation up to the surface. Once at the surface, the formation cuttings and formation fluids may be separated from the drilling fluid for analysis, which is generally performed by personnel stationed at the rig site to continuously monitor and execute the maintenance and adjust the operations of the gas analysis. The drilling fluid may be recirculated in the wellbore.

BRIEF DESCRIPTION OF THE DRAWINGS

Embodiments are described with reference to the following figures. The same numbers are used throughout the figures to reference like features and components. The features depicted in the figures are not necessarily shown to scale. Certain features of the embodiments may be shown exaggerated in scale or in somewhat schematic form, and some details of elements may not be shown in the interest of clarity and conciseness.

DETAILED DESCRIPTION

Figure 1:
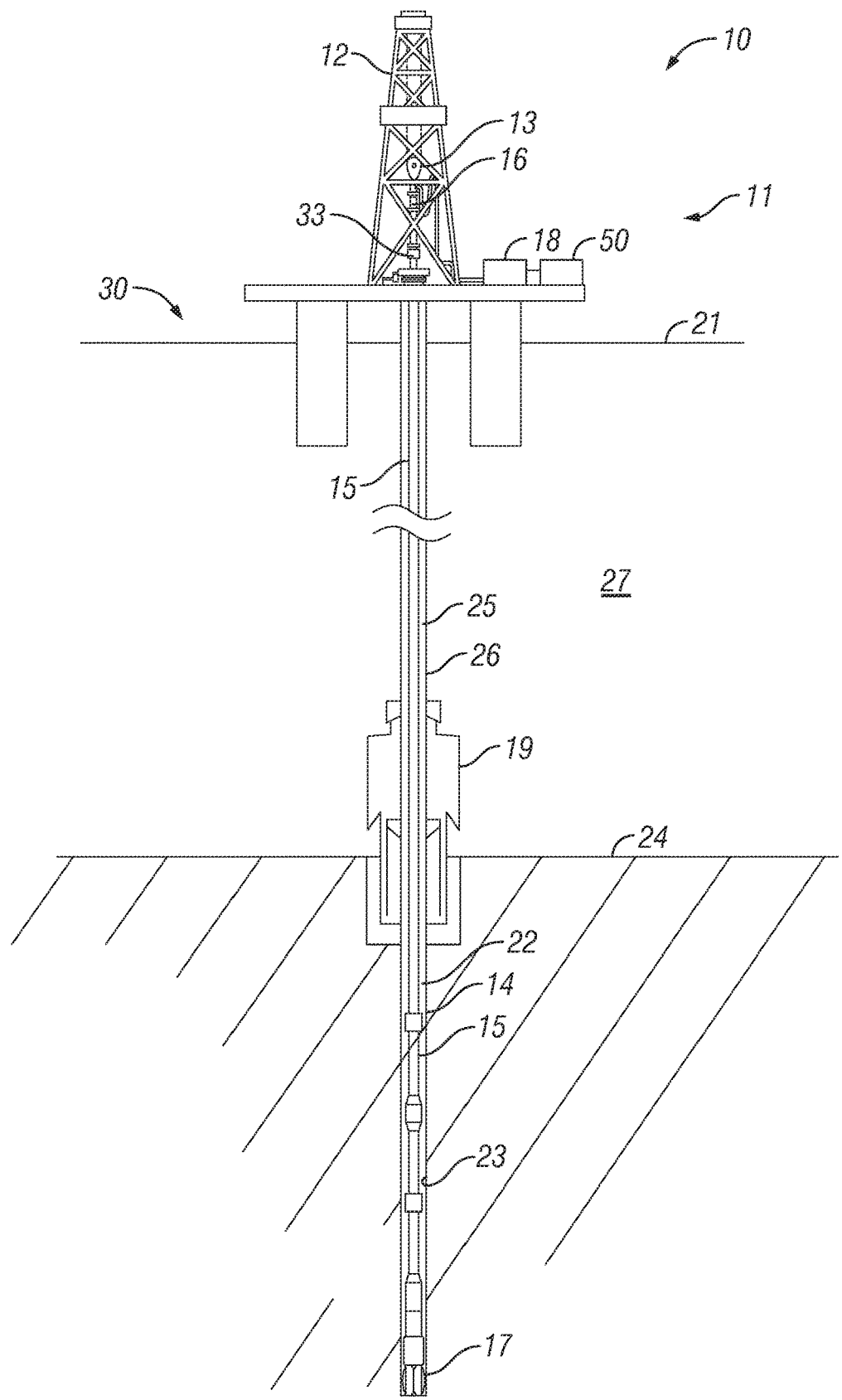
FIG. 1 depicts an elevation view of an offshore drilling platform, according to one or more embodiments.

FIG. 1 shows an elevation view of an offshore drilling system 10 that employs a mud logging system 50 to analyze the gas recovered from the formation by the drilling fluid circulated to the surface. The drilling system 10 comprises an offshore drilling platform (rig) 11 equipped with a derrick 12 that supports a hoist 13. Drilling of oil and gas wells is carried out by a string of drill pipes connected together by "tool" joints 14 so as to form a drill string 15 extending subsea from platform 11. The hoist 13 suspends a kelly 16 used to lower the drill string 15. Connected to the lower end of the drill string 15 is a drill bit 17. The bit 17 is rotated by rotating the drill string 15 and/or a downhole motor (e.g., downhole mud motor).

Drilling fluid, also referred to as drilling "mud," is pumped by mud recirculation equipment 18 (e.g., mud pumps, shakers, etc.) located on the platform 11. The drilling mud is pumped at a relatively high pressure and volume through the drilling kelly 16 and down the drill string 15 to the drill bit 17. The drilling mud exits the drill bit 17 through nozzles or jets in face of the drill bit 17. The mud then returns to the platform 11 at the sea surface 21 via an annulus 22 between the drill string 15 and the borehole 23, through a blowout preventer (BOP) 19 at the sea floor 24, and up an annulus 25 between the drill string 15 and a riser 26 extending through the sea 27 from the blowout preventer 19 to the platform 11. At the sea surface 21, the drilling mud is cleaned and then recirculated by the recirculation equipment 18. The drilling mud is used to cool the drill bit 17, to carry cuttings from the base of the borehole to the platform 11, and to balance the hydrostatic pressure in the rock formations. The mud recirculation equipment 18 is operably connected to a mud logging system 50 to analyze formation fluids recovered from the drilling mud as further described herein with respect to FIG. 2. It should be appreciated that the mud logging system 50 may also be used for drilling systems conducted onshore.

Figure 2:
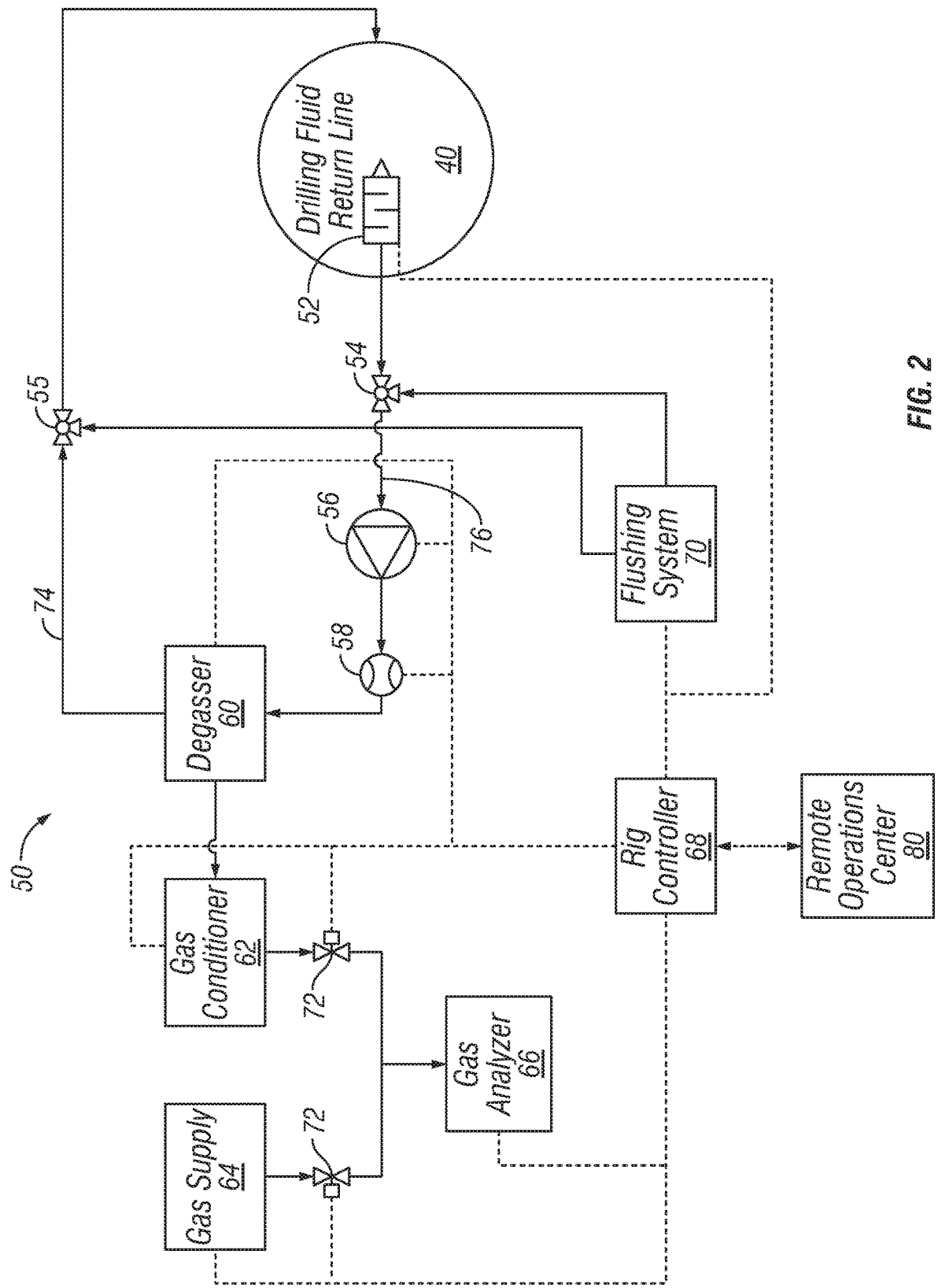
FIG. 2 depicts a schematic view of a mud logging system, according to one or more embodiments.

The mud logging system 50 reduces the mudlogging personnel at the rig site by providing an operations center as further described herein with respect to FIG. 2. The operations center may be located remotely on another offshore platform, an offshore vessel, or onshore allowing the operators to perform remote operational control and maintenance of the mud logging system 50. This enables a reduction in personnel footprint at the offshore platform, which yields a reduction in cost at the offshore platform.

The mud logging system 50 centralizes all control functions and/or system parameters relating to gas analysis and mud logging in one place thereby enabling monitoring, automation, alarm setting, etc. from the operations center. This will lead to a reduction in non-productive time and a more efficient well delivery. The mud logging system 50 may also improve the quality of the gas measurements, as the gas analysis can be autonomously and/or remotely adjusted to ensure the integrity of the gas data.

FIG. 2 shows a schematic view of a mud logging system 50 employed to analyze gas carried to the surface with the drilling fluid, in accordance with one or more embodiments. As shown, the mud logging system 50 includes a probe 52, a mud pump 56, a sensor 58, a degasser 60, a gas conditioner 62, a gas supply 64, a gas analyzer 66, a rig controller 68, a flushing system 70, and a remote operations center 80. All of these components can be located at the drilling rig site (e.g., the drilling platform 11) except for the remote operations center 80. The mud logging system 50 extracts fluid from a drilling fluid return line 40 using the probe 52, which can be a hose or pipe coupled to and in fluid communication with the return line 40. The delivery pump 56 draws some of the drilling fluid out of the return line 40 and directs the drilling fluid to the degasser 60. The return line 40 may be operably connected to the recirculation equipment (18 of FIG. 1) such that the mud logging system 50 may obtain a fluid sample brought to the surface and recirculate any drilling fluid liberated from the gas as further described herein. The pump 56 is also operably connected to the rig controller 68 so that the rig controller 68 may electronically control the operation of the pump 56. The operable connections between the pump 56 and the rig controller 68 may be implemented using any combination of wired or wireless communication interfaces and/or protocols.

In between the mud pump 56 and the degasser 60 is a sensor 58 that measures a parameter of the drilling fluid, including but not limited to the pressure, temperature, density, or flow rate of the drilling fluid. For example, the sensor 58 may be a Coriolis sensor, pressure gauge, temperature sensor, or a flow meter. The sensor 58 is operably connected to the rig controller 68 to provide the rig controller 68 with the measurement data associated with the drilling fluid output by the pump 56. The operable connections between the sensor 58 and the rig controller 68 may be implemented using any combination of wired or wireless communication interfaces and/or protocols. The rig controller 68 may adjust flow rate or pressure of the drilling fluid output by the pump 56 based on the measurements taken by the sensor 58.

The degasser 60 separates air or gases (e.g., methane, $H_2S$, $CO_2$, and others) from the fluid from the pump 56 and may be a vacuum tank degasser or an atmospheric degasser. The degasser 60 provides the separated gas to the gas conditioner 62, which prepares the gas for analysis. The degasser 60 also returns any remaining liquid to the drilling fluid return line 40 to be recirculated through the wellbore. The degasser 60 is also operably connected to the rig controller 68 such that the rig controller 68 can control the operation of the degasser 60. The operable connections between the degasser 60 and the rig controller 68 may be implemented using any combination of wired or wireless communication interfaces and/or protocols.

Figure 3:
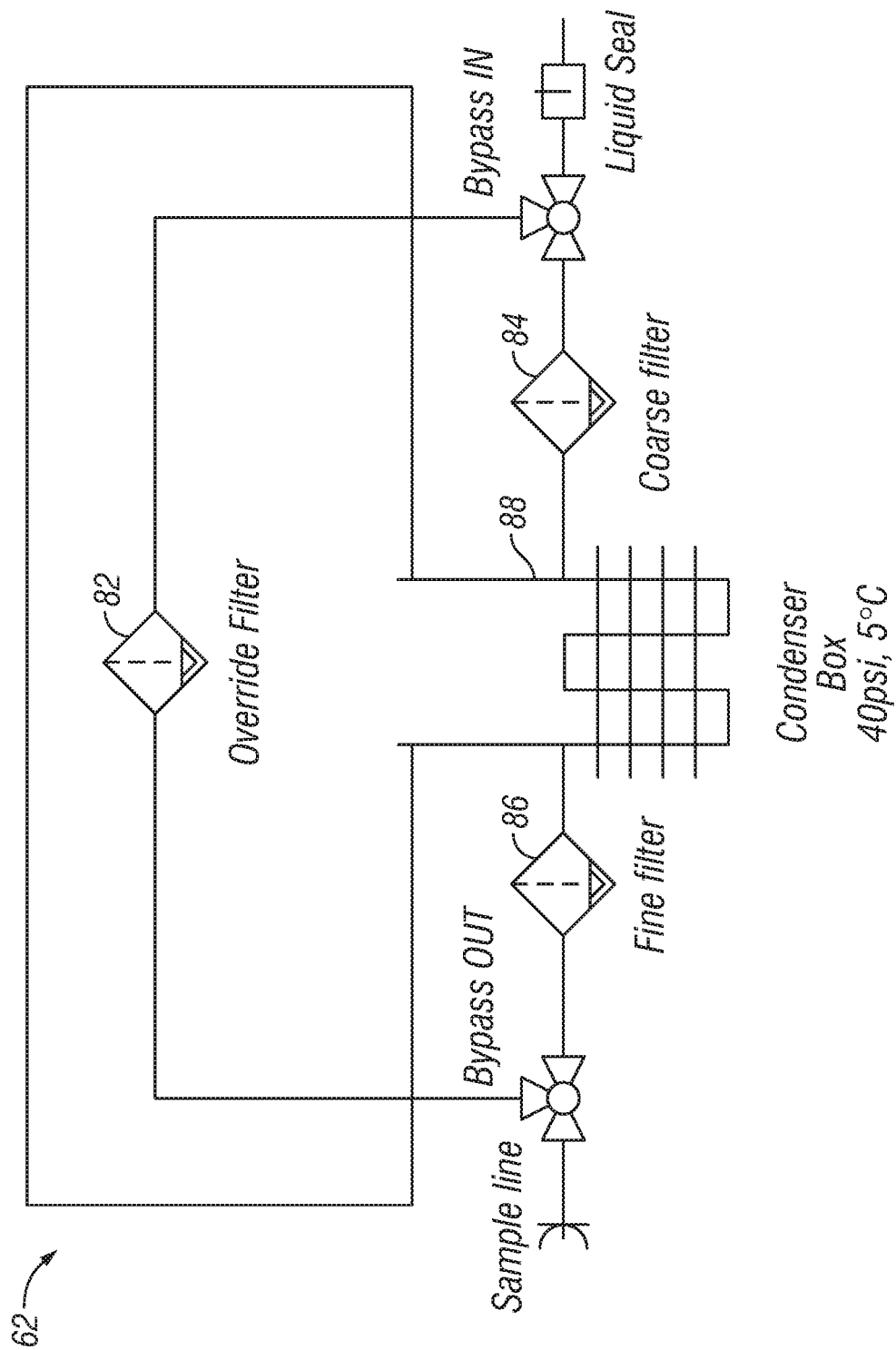
FIG. 3 depicts a schematic view of a gas conditioner, according to one or more embodiments.
Figure 4:
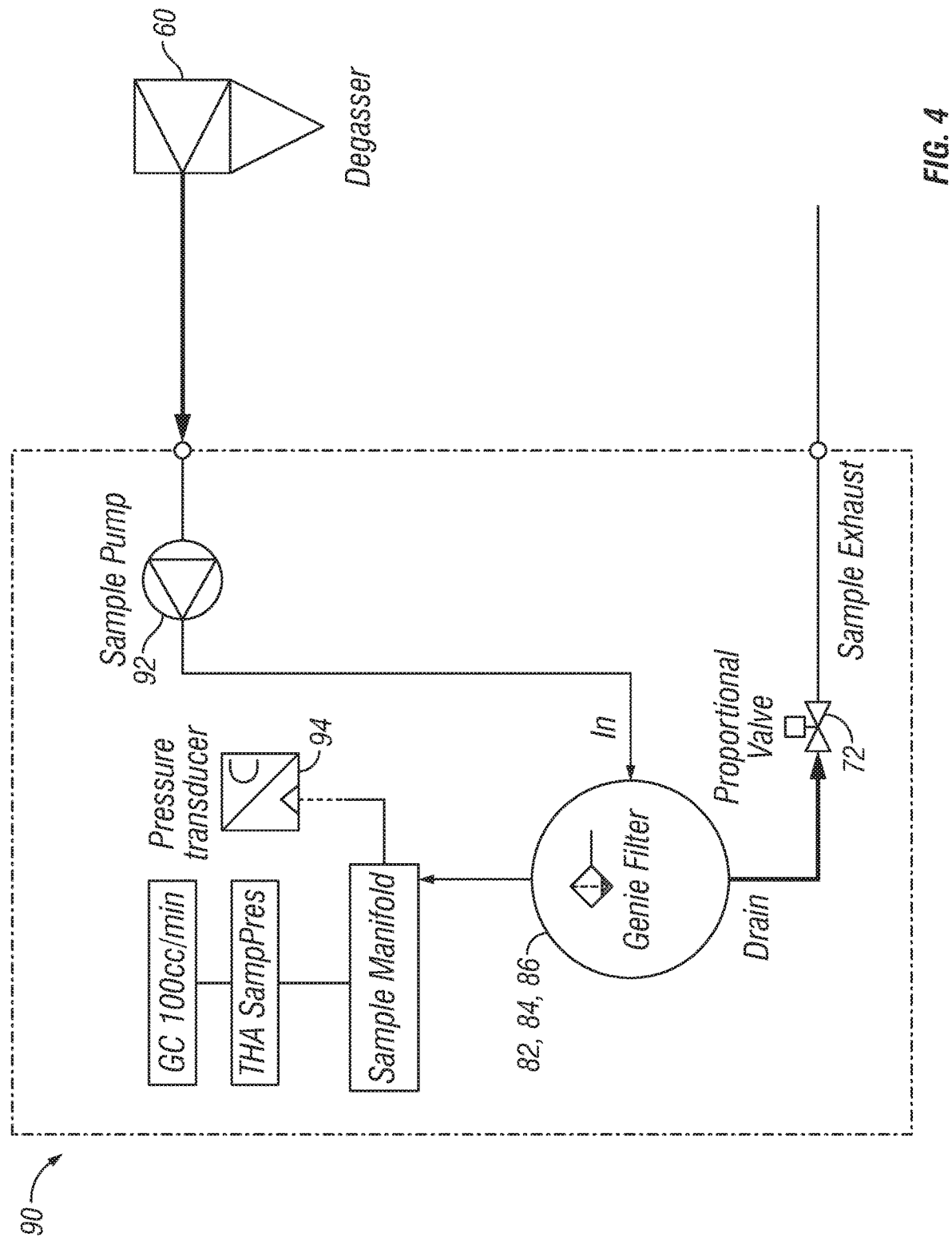
FIG. 4 depicts a schematic view of a filter monitoring system, according to one or more embodiments.

The gas conditioner 62 passes the gas through various filters and a condenser (not shown) as further described herein with respect to FIGS. 3 and 4. The gas conditioner 62 removes stray solids in the gas and condensate and other moisture from the gas. The gas conditioner 62 is operably electronically connected to the rig controller 68 such that the rig controller 68 can control the operation of the gas conditioner 62. The operable connections between the gas conditioner 62 and the rig controller 68 may be implemented using any combination of wired or wireless communication interfaces and/or protocols. This connection allows the rig controller 68 to monitor the operational status of the gas conditioner 62, including but not limited to a flow rate or pressure of the gas sample supplied to the gas analyzer 66 or identifying that filters in the gas conditioner 62 require replacement, as further described herein with respect to FIG. 4. Additionally, the rig controller 62 may transmit an alert signal to the remote operations center 80 after determining that a filter needs replacement. The remote operations center 80 then may instruct personnel at the rig site to replace the filters of the gas conditioner 62.

The gas conditioner 62 passes the gas sample to the gas analyzer 66 to determine a property of the gas. The gas analyzer 66 may analyze the composition of the extracted gas for the concentration of gases of interest and the amount of total gas. The property of the gas may include a chemical composition of the gas, the total amount of combustible gas, physical properties of the gas, moisture content of the gas, or the like. The gas analyzer 66 may include one or more gas analyzers include but not limited to a total gas analyzer (TGA), also referred to as a total hydrocarbon analyzer (THA), a gas chromatograph (GC), a mass spectrometer, an infrared spectrometer, an isotopic analyzer, or any other suitable analyzer. The TGA measures the total amount of gas, typically the total amount of combustible gas. The usual unit of TGA measurement is total methane equivalents (TME), which is essentially the BTU content of the gas extracted from the drilling fluid, expressed as that which would be obtained from an equivalent concentration of pure methane in air. The TGA, while giving an undifferentiated indication of gas entrained in the drilling fluid, has the advantage of operating in a continuous mode. The TGA may use either a thermal conductivity detector (TCD) or a flame ionization detector (FID).

The gas supply 64 holds a calibration gas or any other suitable gas and provides this gas to the gas analyzer 66. The gasses held in the gas supply may include methane, $H_2$, nitrogen, or any other suitable gas. The gas supply 64 may also include a gas generator such as a hydrogen gas generator, a nitrogen gas generator, or a zero air generator. The calibration gas may be used to calibrate the gas analyzer 66. For instance, the gas analyzer 66 may compare the response of the calibration gas to the response of the gas recovered from the wellbore with the drilling fluid under the various analysis methods to determine a property of the gas.

The gas supply 64 may also provide a carrier gas (e.g., nitrogen or zero air) to pass the gas sample to the gas analyzer 66. The carrier gas and gas sample are mixed to provide a makeup gas with a controlled flow. The makeup gas flow rate depends on concentration of the gas sample. The rig controller 68 may respond to the concentration of the gas sample. To get a higher resolution on low gas concentrations, the makeup gas flow may be reduced, e.g., from 3 l/min to 1.5 l/min. To get a higher resolution on higher gas concentrations, the makeup gas may be increased, e.g., from 3 l/min to 6 l/min A low gas concentration may be, for example, 2% methane equivalent. A medium gas concentration may be, for example, 20% methane equivalent. A higher gas concentration may be, for example, 200% methane equivalent.

Each gas analyzer 66 may receive the gas sample and/or the calibration gas via separate flow channels (not shown) and may also require a different flow rate and/or pressure to receive the gas sample and/or the calibration gas. As such, the rig controller 68 adjusts a parameter of the gas sample and/or the calibration gas supplied to the gas analyzer 66, including but not limited to a flow rate or pressure of the gas sample, using the control valves 72 as further described herein with respect to FIG. 5.

The rig controller 68 also autonomously operates the various functions of the mud logging system 50. The rig controller 68 may be a computing system having a processor and storage as further described herein with respect to FIG. 7. For example, the rig controller 68 may adjust the flow rate or pressure of the drilling fluid output by the pump 56. The rig controller 68 may initiate a vibrate sequence or blowback sequence on the probe 52 to clean the probe 52. The rig controller 58 may identify that mud logging system 50 needs to be cleaned using the flushing system 70 as further described herein. The rig controller 62 may identify that the filters used in the gas conditioner 62 are clogged and need to be replaced. The rig controller 68 is located at the rig site, such as the offshore drilling platform 11 of FIG. 1.

The flushing system 70 may be used to clean flow lines 74 and 76, the pump 56, or the degasser 60. The flushing system 70 is in fluid communication with the pump 56 and degasser 60 via valves 54 and 55 and the flow lines 74 and 76. The flushing system 70 is used to inject a flushing fluid into the flow lines 74 and 76 to rid these flow lines, the pump 56, or the degasser 60 of any solids that may clog the mud logging system 50. For instance, when fluid analysis is paused, the drilling fluid or particulates in the drilling fluid may deposit or harden in the degasser 60 reducing the efficiency of the degasser. To clean the mud logging system 50, the rig controller 68 may close off flow from the drilling fluid return line 40 at the valve 54 and close off the return path from the degasser at the valve 55. The flushing system 70 then may inject oil-free compressed air in the reverse direction of the flow of the drilling fluid through the valve 55 into the flow line 74. The reverse injection will blow back any debris in the flow line 74 into the degasser 60. As previously mentioned, the gas conditioner 62 is equipped with suitable filters to prevent any debris from entering the gas analyzer 66. The rig controller 68 may also instruct the gas conditioner 62 to drain any moisture while operating in reverse flow to ensure automated filter maintenance as well. It should be appreciated that the flushing system 70 may be in fluid communication with any other suitable component of the mud logging system to facilitate cleaning the mud logging system as described herein.

The flushing system 70 may also remove moisture or water droplets by injection of a glycol in the reverse flow direction into the sample line. The injected glycol is blown by means of oil-free compressed air back into the degasser 60. The flushing fluid may include a glycol or oil-free air. The flushing system 70 may include a pump and a supply of the flushing fluid in fluid communication with the valves 54 and 55.

The remote operations center 80 provides a remote-control center for operating and monitoring the mud logging system 50. The remote operations center 80 is not located at the rig site and may be located onshore in the case of an offshore drilling platform (11 of FIG. 1). The remote operations center 80 may also be located on other offshore platforms or vessels. The remote operations center 80 includes a computing system that provides an operational dashboard to mud logging personnel as further described herein with respect to FIGS. 6 and 7. The operational dashboard provides operational information about the mud logging system 50, including but not limited to measurements taken by the sensor 58 or the properties of the gas ascertained by the gas analyzer 66. The operational dashboard may also allow personnel to adjust the settings of the mud logging system 50, for example, selecting the type of gas analyzer to receive the gas sample, selecting the flow rate of the gas sample supplied to the gas analyzer, etc. The remote operations center 80 then transmits a control signal to the rig controller 68 to adjust the settings of the mud logging system 50.

As previously mentioned, the mud logging system may employ a gas conditioner to filter and condense the gas sample. For example, FIG. 3 shows a schematic view of an example gas conditioner 62, in accordance with one or more embodiments. The gas conditioner 62 passes the sample through filters 82, 84, and 86 as well as a condenser 88. The filter 82 may be an override filter used in situations where the flow path through the filters 84 and 86 and the condenser may be unavailable. For instance, the override filter may be used while replacing the filters 84 and 86 or while the flushing system 70 is used to clean out the mud logging system 50.

As previously discussed, the rig controller may also monitor the filters for any clogs and identify filters for replacement. For example, FIG. 4 shows a schematic view of a filter monitoring system 90 that may be integrated with the gas conditioner 62 to monitor the operational state of the filters of the gas conditioner. The filter monitoring system 90 includes a sample pump 92 and a sensor 94. The sample pump 92 directs the gas sample to the filter 82, 84, 86 at a pre-determined pressure or flow rate. The sensor 94 is in fluid communication with the filter 82, 84, 86 to measure the flow rate or pressure of the gas sample. The rig controller may identify that the filter is clogged if the flow rate measured by the sensor 94 drops below a threshold flow rate value.

Figure 5:
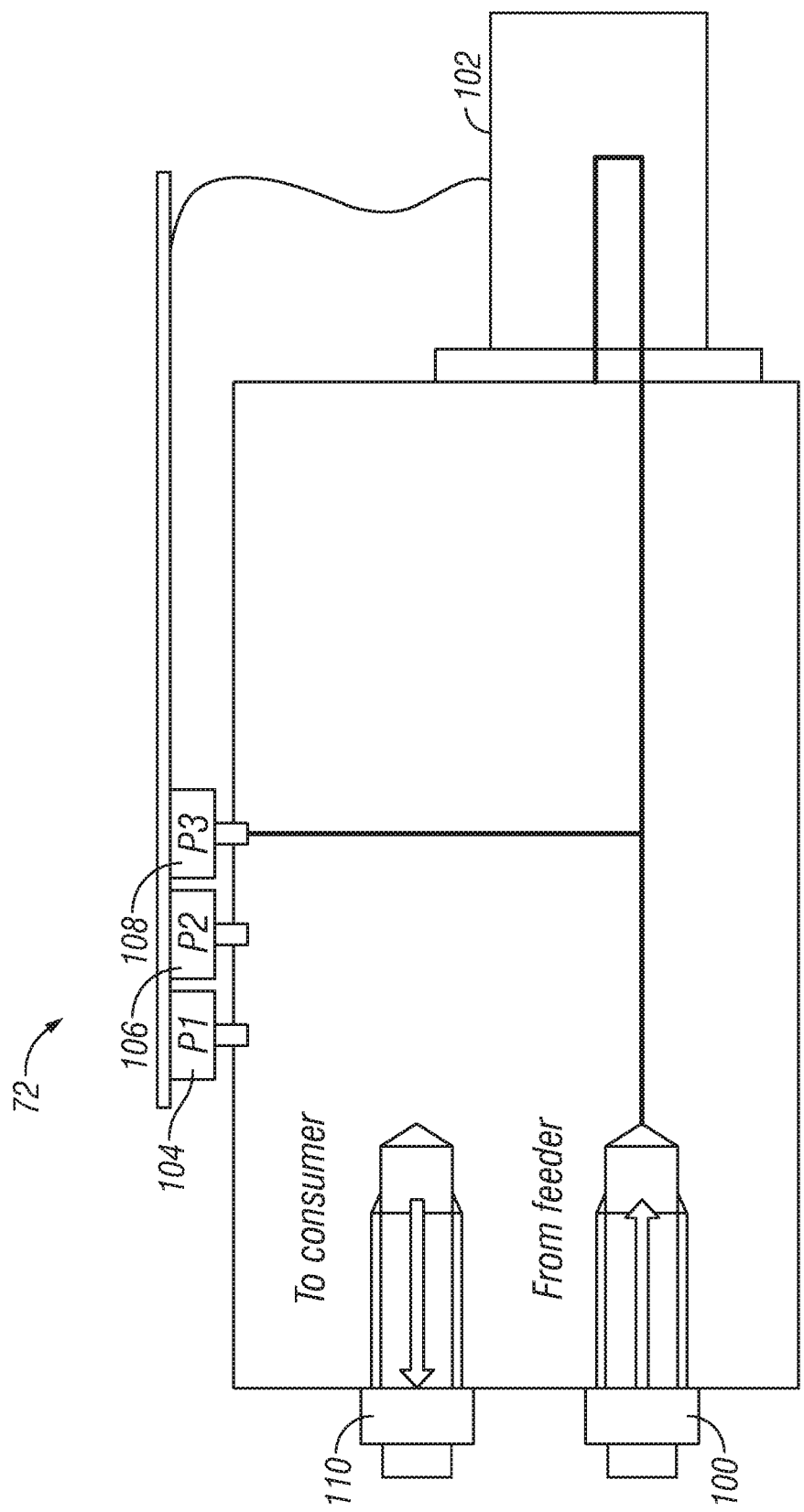
FIG. 5 depicts a schematic view of a control valve, according to one or more embodiments.

As previously discussed, the rig controller may adjust a parameter of the gas sample or the calibration fluid via control valves (72 of FIG. 2) depending on the gas analyzer selected for analysis. FIG. 5 shows a schematic view of a control valve 72 employed to adjust the flow rate or pressure of the fluid supplied to the gas analyzer, in accordance with one or more embodiments. The control valve 72 may include an inlet 100; a proportional pressure valve 102; pressure sensors 104, 106, 108; and an outlet 110. The fluid enters through the inlet 100 and passes through the proportional pressure valve 102. The control valve 72 provides pressure measurements from the pressure sensors 104, 106, 108 so that the flow rate or the pressure output from the outlet 110 can be derived using Bernoulli's principle and the Venturi effect encountered in the control valve. The pressure output by the proportional valve 102 is adjusted to reach the desired flow rate or pressure from the outlet based on the pressure readings taken from the pressure sensors 104, 106, and 108.

Figure 7:
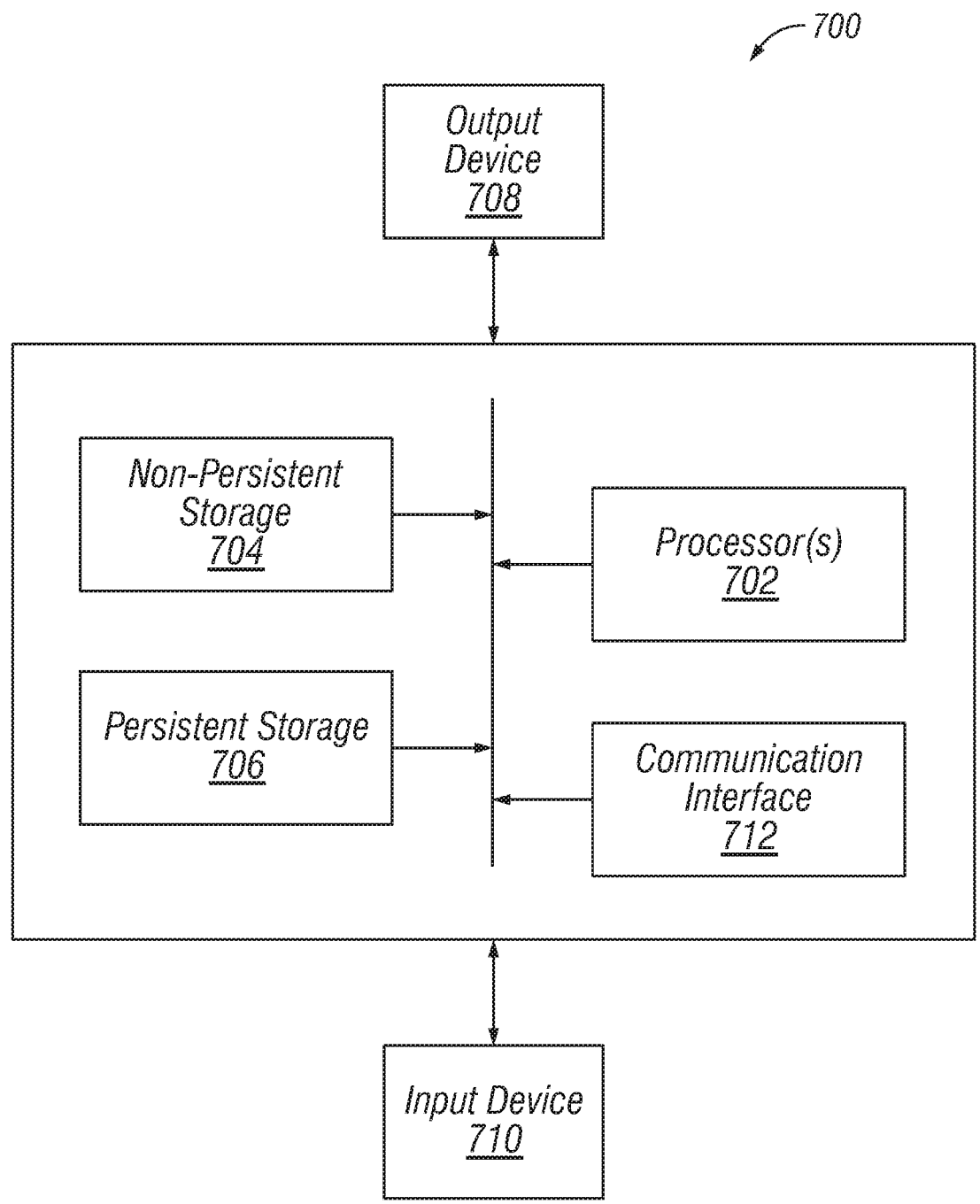
FIG. 7 depicts a block diagram view of a computing system, according to one or more embodiments.

A computing system as further described herein with respect to FIG. 7 is provided to allow personnel to operate and manage the mud logging system (50 of FIGS. 1 and 2). The mud logging system is computer controlled which enables the automation of the gas analysis and remote monitoring of the gas analysis. The computing system may control the pumps, motors, valves, pressures, flow rates, temperatures, densities, gas extraction, gas conditioning, etc. of the mud logging system enabling algorithms to monitor its performance and maintenance. The computerized system can maintain a suitable environment for gas extraction and gas analysis. The computing system may also provide pre-programmed functions for performing maintenance or operations on the mud logging system. For instance, the pre-programmed functions may include cleaning the components of the mud logging system by means of compressed air; cleaning the components of the mud logging system by means of injecting of flushing fluid (glycol); selecting channels for pressure regulated gases (forward and backward pressure setup); selecting the channels for flow regulated gases; conditioning of the analyte with regards to particle size and moisture; and automated calibration and verification of gas analyzers.

Figure 6:
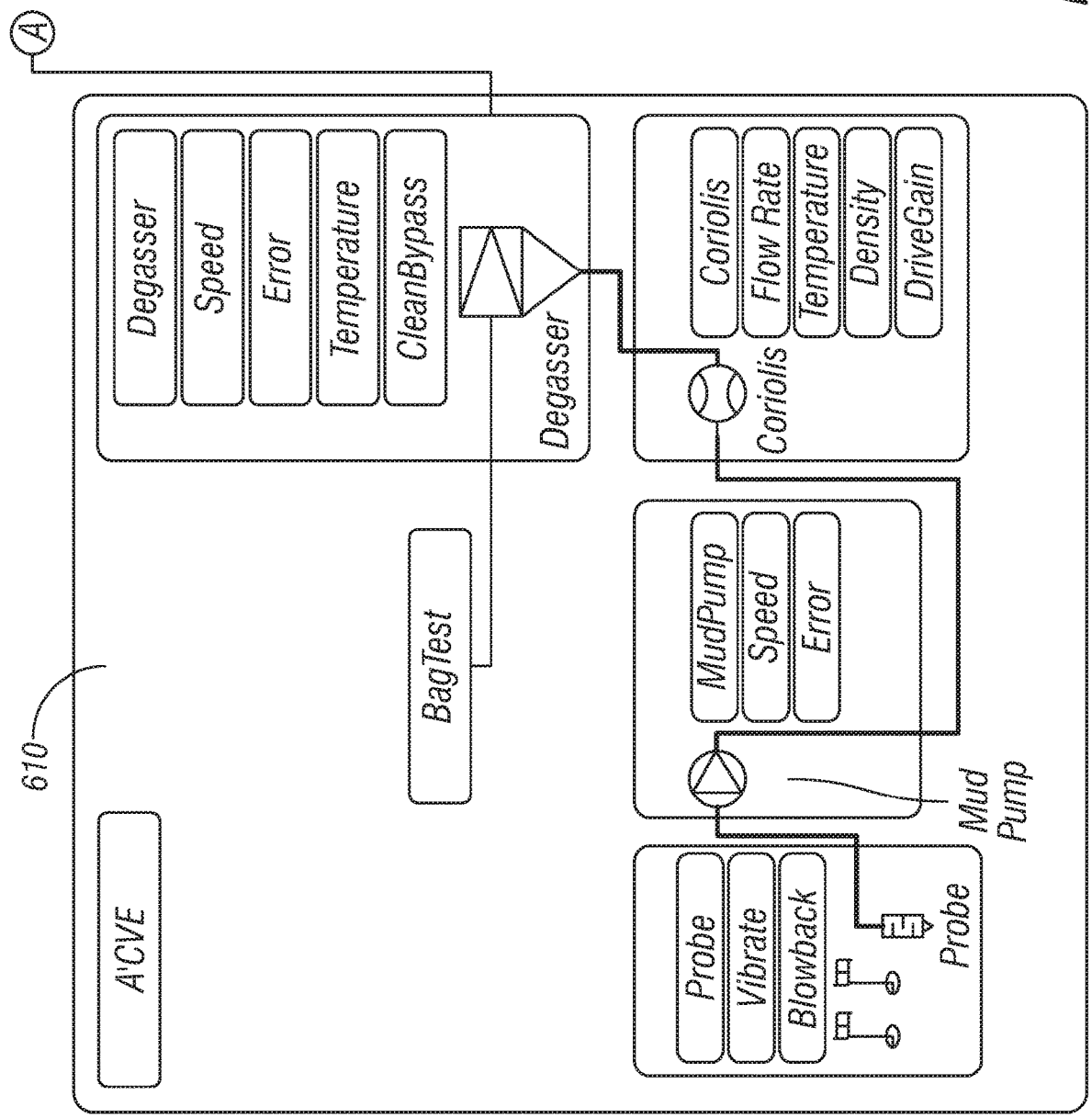
FIG. 6 depicts diagram view of an operations and maintenance dashboard, according to one or more embodiments.
Figure 6:
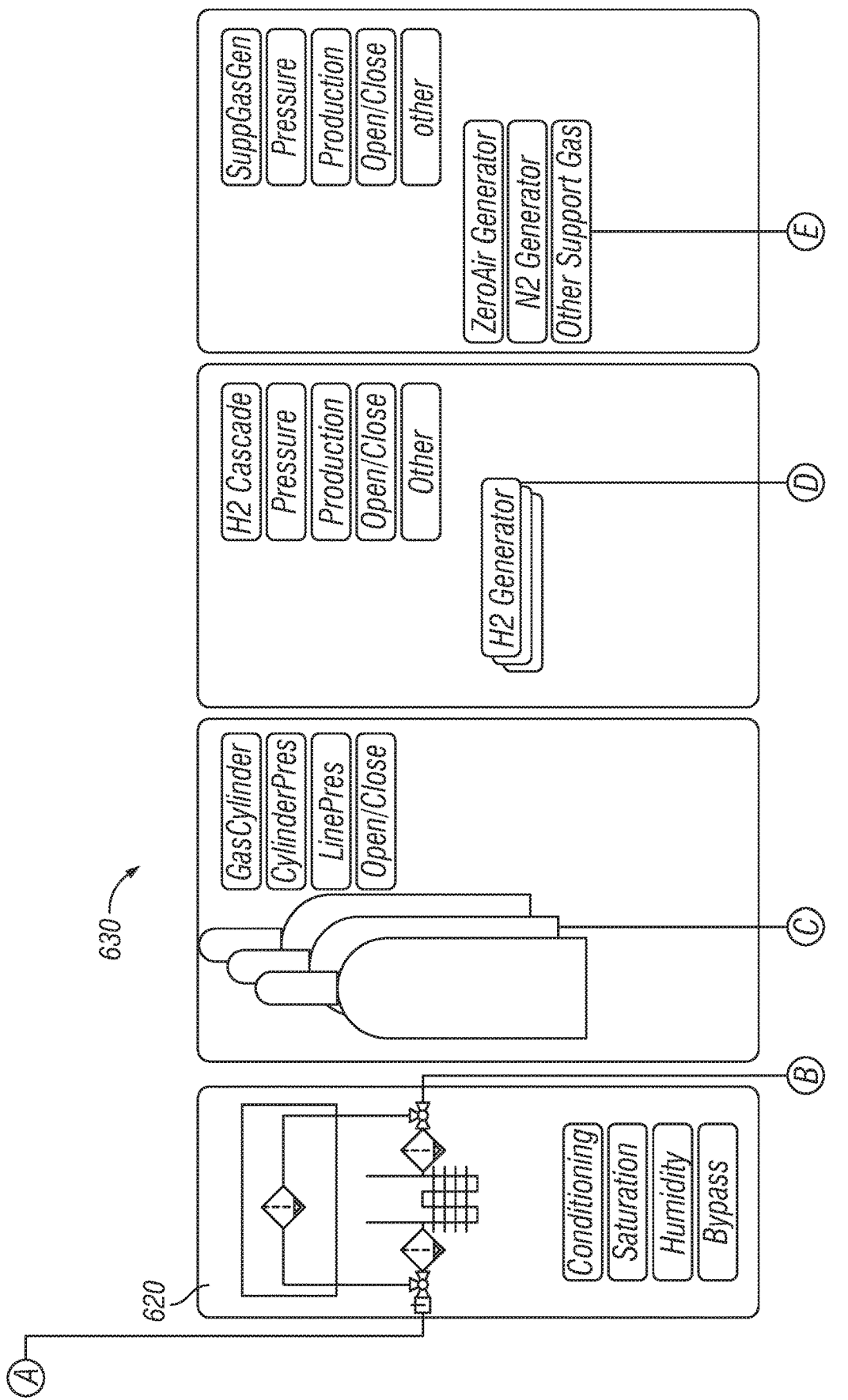
Figure 6:
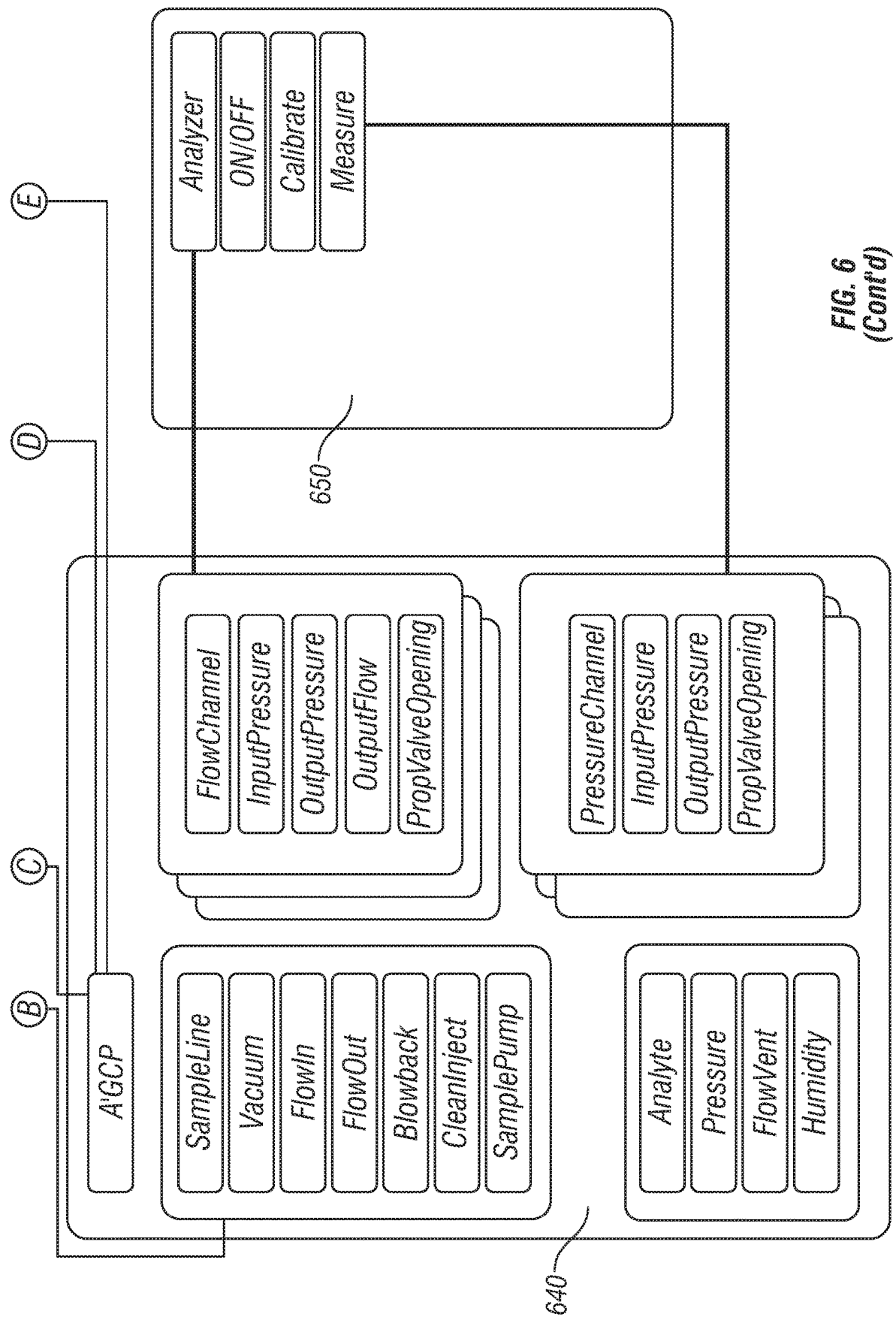

The computing system includes input and output devices that allow the personnel to interact with a visual representation (such as a dashboard) of the mud logging system. For example, FIG. 6 shows a diagram view of an operations and monitoring dashboard 600, in accordance with one or more embodiments. As shown, the dashboard 600 includes a gas extraction module 610, a gas conditioner module 620, a gas supply module 630, a gas sample module 640, and a gas analyzer module 650. The dashboard 600 may be presented to the personnel on an output device of the computing system, and the personnel may obtain operational information associated with the gas analysis or adjust the operations of the gas analysis by interacting with the dashboard using an input device of the computing system.

The gas extraction module 610 provides information and controls to adjust the process of extracting gas from the drilling fluid. The gas extraction module 610 may include controls for the probe to initiate a vibration sequence or blowback sequence to clean the probe. The gas extraction module 610 may also provide operational information related to the pump, sensor, and degasser, including but not limited to the speed of the mud pump, any errors with the mud pump, the flow rate of the drilling fluid, the temperature of the drilling fluid, the density of the drilling fluid, the speed of the degasser, any errors with the degasser, the temperature of the degasser. The gas extraction module 610 may also provide controls to clean the degasser as described herein with respect to FIG. 2.

The gas conditioner module 620 provides operational information associated with the gas conditioner. The gas conditioner module 620 may provide information about the saturation of the filters and the humidity of the gas sample. The gas conditioner module 620 may also provide a control to bypass the main filters to pass the gas sample through the override filter as described herein with respect to FIG. 3.

The gas supply module 630 provides controls and information related to the gas supplies of the mud logging system. The gas supply module 630 may provide operational information such as the cylinder pressure, the outlet line pressure, or the status of producing the gas (e.g., $H_2$ or $N_2$). The gas supply module 630 may also provide controls for opening/closing valves to release gas from the supply or shut-off the gas supplies.

The gas sample module 640 provides controls to perform maintenance or adjust the flow of the gas supplied to the gas analyzer. The gas sample module 640 may provide functions for performing maintenance on the flow line between the gas conditioner and the gas analyzer, including but not limited to generating a partial vacuum on the flow line, reversing the flow, injecting a flushing fluid, or controlling a sample pump. The gas sample module 640 may also provide controls for selecting the channel for gas analysis, such as the flow rate dependent channels or the pressure dependent channels. For these channels, the gas sample module 640 may provide controls to adjust the pressure or flow rate of the gas sample supplied to the gas analyzer.

The gas analyzer module 650 provides controls to control the operations of the gas analyzer. The gas analyzer module 650 provides controls to select the type of gas analysis to be performed, to calibrate the corresponding gas analyzer, and to take the measurements of the gas analyzer.

FIG. 7 shows a diagram view of a computing system in accordance with one or more embodiments. The computing system 700 may include one or more computer processors 702, non-persistent data storage 704 (e.g., volatile memory, such as random access memory (RAM), cache memory), persistent data storage 706 (e.g., a hard disk, an optical drive such as a compact disk (CD) drive or digital versatile disk (DVD) drive, a flash memory, etc.), a communication interface 712 (e.g., Bluetooth interface, infrared interface, network interface, optical interface, etc.), input devices 710, output devices 708, and numerous other elements (not shown) and functionalities. Each of these components is described below.

The computer processor(s) 702 may be an integrated circuit for processing instructions. For example, the computer processor(s) may be one or more cores or micro-cores of a processor. The computing system 700 may also include one or more input devices 710, such as a touchscreen, keyboard, mouse, microphone, touchpad, electronic pen, or any other type of input device. Further, the communication interface 712 may include an integrated circuit for connecting the computing system 700 to a network (not shown) (e.g., a local area network (LAN), a wide area network (WAN) such as the Internet, mobile network, or any other type of network) and/or to another device, such as another computing system.

The computing system 700 may also include one or more output devices 708, such as a screen (e.g., a liquid crystal display (LCD), a plasma display, touchscreen, cathode ray tube (CRT) monitor, projector, or other display device), a printer, external storage, or any other output device. One or more of the output devices may be the same or different from the input device(s). The input and output device(s) may be locally or remotely connected to the computer processor(s) 702, non-persistent storage 704, and persistent storage 706. Many different types of computing systems exist, and the aforementioned input and output device(s) may take other forms.

In addition to the embodiments described above, many examples of specific combinations are within the scope of the disclosure, some of which are detailed below:

Example 1

A system for analyzing a gas in a drilling fluid, comprising: a degasser operable to separate the gas from the drilling fluid; a gas analyzer in fluid communication with the degasser to receive a sample of the separated gas and operable to determine a property of the gas; and a controller in communication with the gas analyzer and operable to automate the operation of the gas analyzer by adjusting a parameter of the separated gas sample as the gas sample is supplied to the gas analyzer.

Example 2

The system of Example 1, wherein the parameter is selected from the group consisting of a flow rate, pressure, temperature, and concentration of the separated gas.

Example 3

The system of Example 1, further comprising a flushing system operable to inject a flushing fluid into the degasser.

Example 4

The system of Example 1, further comprising a gas supply comprising a calibration gas in fluid communication with the gas analyzer, wherein the controller is further operable to adjust a flow rate or a pressure of the calibration gas supplied to the gas analyzer.

Example 5

The system of Example 1, further comprising a gas conditioner operable to filter and remove moisture from the separated gas before the gas is supplied to the gas analyzer, wherein the controller is further operable to monitor the operation of the gas conditioner.

Example 6

The system of Example 1, further comprising a control valve operable to adjust a flow rate or a pressure of the separated gas sample supplied to the gas analyzer from the degasser.

Example 7

The system of Example 1, further comprising a pump in fluid communication with a return line for the drilling fluid and operable to inject drilling fluid into the degasser, wherein the controller is further operable to adjust a flow rate of the drilling fluid output by the pump.

Example 8

The system of Example 7, further comprising a flushing system operable to inject a flushing fluid into the pump.

Example 9

The system of Example 1, further comprising a sensor between the degasser and the pump, wherein the controller is further operable to receive fluid measurements from the sensor.

Example 10

The system of Example 1, further comprising a probe in fluid communication with a return line for the drilling fluid, wherein the controller is further operable to initiate a vibration sequence and a blowback sequence for the probe.

Example 11

The system of Example 1, further comprising a computing system in communication with the controller and operable to receive operational information associated with the gas analysis and transmit a control signal to the controller to adjust the parameter.

Example 12

A method of analyzing a gas in a drilling fluid, comprising: separating a sample of the gas from the drilling fluid using a degasser; adjusting a parameter of the separated gas sample autonomously, using a controller; supplying the separated gas sample to a gas analyzer; and determining a property of the separated gas sample using the gas analyzer.

Example 13

The method of Example 12, wherein the parameter is selected from the group consisting of a flow rate, pressure, temperature, and concentration of the separated gas.

Example 14

The method of Example 12, further comprising injecting a flushing fluid into the degasser using a flushing system.

Example 15

The method of Example 12, further comprising adjusting a flow rate or a pressure of a calibration gas supplied to the gas analyzer using the controller.

Example 16

The method of Example 12, further comprising conditioning the separated gas sample, using a gas conditioner, before the gas sample is supplied to the gas analyzer.

Example 17

The method of Example 12, wherein adjusting the parameter of the separated gas sample comprises adjusting a flow rate or a pressure of the separated gas sample using a control valve between the degasser and the gas analyzer.

Example 18

The method of Example 12, further comprising pumping the drilling fluid, using a pump, from a return line to the degasser.

Example 19

The method of Example 18, further comprising injecting a flushing fluid into the pump using a flushing system.

Example 20

The method of Example 12, further comprising: receiving operational information associated with the gas analysis at a computing device in communication with the controller; and transmitting control signal to the controller to adjust the parameter.

This discussion is directed to various embodiments of the present disclosure. The drawing figures are not necessarily to scale. Certain features of the embodiments may be shown exaggerated in scale or in somewhat schematic form and some details of conventional elements may not be shown in the interest of clarity and conciseness. Although one or more of these embodiments may be preferred, the embodiments disclosed should not be interpreted, or otherwise used, as limiting the scope of the disclosure, including the claims. It is to be fully recognized that the different teachings of the embodiments discussed may be employed separately or in any suitable combination to produce desired results. In addition, one skilled in the art will understand that the description has broad application, and the discussion of any embodiment is meant only to be exemplary of that embodiment, and not intended to suggest that the scope of the disclosure, including the claims, is limited to that embodiment.

Certain terms are used throughout the description and claims to refer to particular features or components. As one skilled in the art will appreciate, different persons may refer to the same feature or component by different names. This document does not intend to distinguish between components or features that differ in name but not function, unless specifically stated. In the discussion and in the claims, the terms "including" and "comprising" are used in an open-ended fashion, and thus should be interpreted to mean "including, but not limited to . . . ." Also, the term "couple" or "couples" is intended to mean either an indirect or direct connection. In addition, the terms "axial" and "axially" generally mean along or parallel to a central axis (e.g., central axis of a body or a port), while the terms "radial" and "radially" generally mean perpendicular to the central axis. The use of "top," "bottom," "above," "below," and variations of these terms is made for convenience, but does not require any particular orientation of the components.

Reference throughout this specification to "one embodiment," "an embodiment," or similar language means that a particular feature, structure, or characteristic described in connection with the embodiment may be included in at least one embodiment of the present disclosure. Thus, appearances of the phrases "in one embodiment," "in an embodiment," and similar language throughout this specification may, but do not necessarily, all refer to the same embodiment.

Although the present disclosure has been described with respect to specific details, it is not intended that such details should be regarded as limitations on the scope of the disclosure, except to the extent that they are included in the accompanying claims.

What is claimed is:

1. A system for analyzing a gas in a drilling fluid, comprising:
    a degasser operable to separate the gas from the drilling fluid to produce a separated gas sample comprising gas only from the drilling fluid;
    a gas conditioner comprising a condenser to condense the separated gas sample and filters to filter solids, condensate, and other moisture from the separated gas sample to produce a separated, conditioned gas sample;
    a gas analyzer in fluid communication with the gas conditioner to receive the separated, conditioned gas sample and operable to determine a property of the gas;
    a controller in communication with the gas analyzer and operable to automate operation of the gas analyzer and the degasser by adjusting a parameter of the separated gas sample or the separated, conditioned gas sample and monitor and control the operation of the gas conditioner for performing maintenance; and
    a remote operations center comprising a computing system in communication with the controller and operable to receive operational information associated with the gas analyzer and remotely monitor and control the controller to adjust the parameter.

2. The system of claim 1, wherein the parameter is selected from the group consisting of a flow rate, pressure, temperature, and concentration.

3. The system of claim 1, further comprising a flushing system controllable by the controller and operable to inject a flushing fluid into the degasser.

4. The system of claim 1, further comprising a gas supply comprising a calibration gas in fluid communication with the gas analyzer bypassing the gas conditioner, wherein the controller is further operable to adjust a flow rate or a pressure of the calibration gas supplied to the gas analyzer.

5. The system of claim 1, further comprising a control valve operable to adjust a flow rate or a pressure of the separated, conditioned gas sample supplied to the gas analyzer from the gas conditioner.

6. The system of claim 1, further comprising a pump in fluid communication with a return line for the drilling fluid and operable to inject drilling fluid into the degasser, wherein the controller is further operable to adjust a flow rate of the drilling fluid output by the pump.

7. The system of claim 6, further comprising a flushing system operable to inject a flushing fluid into the pump.

8. The system of claim 6, further comprising a sensor between the degasser and the pump, wherein the controller is further operable to receive fluid measurements from the sensor.

9. The system of claim 1, further comprising a probe in fluid communication with a return line and operable to extract the drilling fluid, wherein the controller is further operable to initiate a vibration sequence and a blowback sequence to clean the probe.

10. The system of claim 1, wherein the gas conditioner further comprises an override filter in a bypass line that bypasses the filters and the condenser such that the filters may be replaced.

11. A method of analyzing a gas in a drilling fluid, comprising:
    separating a sample of the gas from the drilling fluid using a degasser to produce a separated gas sample comprising gas only from the drilling fluid;
    conditioning the separated gas sample using a gas conditioner comprising filters to remove solids from and a condenser located between the filters to remove condensate and other moisture from the separated gas sample to produce a separated, conditioned gas sample;
    supplying the separated, conditioned gas sample to a gas analyzer;
    determining a property of the separated gas sample using the gas analyzer;
    automating the operation of the gas analyzer and the degasser by adjusting a parameter of the separated gas sample or the separated, conditioned gas sample using a controller;
    monitoring and controlling operation of the gas conditioner for performing maintenance using the controller; and
    receiving operational information associated with the gas analyzer and remotely monitoring and controlling the controller to adjust the parameter using a remote operations center.

12. The method of claim 11, wherein the parameter is selected from the group consisting of a flow rate, pressure, temperature, and concentration.

13. The method of claim 11, further comprising controlling a flushing system with the controller to inject a flushing fluid into the degasser.

14. The method of claim 11, further comprising adjusting a flow rate or a pressure of a calibration gas supplied to the gas analyzer bypassing the gas conditioner using the controller.

15. The method of claim 11, wherein adjusting the parameter of the separated gas sample comprises adjusting a flow rate or a pressure of the separated, conditioned gas sample using a control valve between the gas conditioner and the gas analyzer.

16. The method of claim 11, further comprising:
    pumping the drilling fluid, using a pump, from a return line to the degasser; and
    controlling the pump with the controller to adjust a flow rate of the drilling fluid output by the pump.

17. The method of claim 16, further comprising injecting a flushing fluid into the pump using a flushing system.

18. The method of claim 11, further comprising:
bypassing the separated gas sample from the filters in the gas conditioner to instead flow through an override filter in the gas conditioner; and
replacing the filters in the gas conditioner.

19. The method of claim 16, further comprising the controller receiving fluid measurements from a sensor between the degasser and the pump.

20. The method of claim 11, further comprising:
extracting the drilling fluid from a drilling fluid return line using a probe; and
cleaning the probe using the controller to initiate a vibration sequence and a blowback sequence for the probe.

* * * * *